United States Patent
Gaissmaier et al.

(10) Patent No.: US 11,324,855 B2
(45) Date of Patent: May 10, 2022

(54) CELL-FREE COMBINATION, HYDROGEL-LIKE MATERIAL OR HYDROGEL AND USE OF SAME

(71) Applicant: TETEC TISSUE ENGINEERING TECHNOLOGIES AG, Reutlingen (DE)

(72) Inventors: Christoph Gaissmaier, Kusterdingen (DE); Nils Clausen, Tuebingen (DE); Karin Benz, Goeppingen (DE)

(73) Assignee: TETEC Tissue Engineering Technologies AG, Reutlingen (DE)

( * ) Notice: Subject to any disclaimer, the term of this patent is extended or adjusted under 35 U.S.C. 154(b) by 0 days.

(21) Appl. No.: 16/609,041

(22) PCT Filed: Apr. 24, 2018

(86) PCT No.: PCT/EP2018/060486
§ 371 (c)(1),
(2) Date: Oct. 28, 2019

(87) PCT Pub. No.: WO2018/197500
PCT Pub. Date: Nov. 1, 2018

(65) Prior Publication Data
US 2020/0147263 A1  May 14, 2020

(30) Foreign Application Priority Data

Apr. 26, 2017  (DE) .................. 10 2017 207 049.8

(51) Int. Cl.
| | | |
|---|---|---|
| *A61L 27/34* | (2006.01) | |
| *A61L 27/22* | (2006.01) | |
| *A61L 27/52* | (2006.01) | |
| *A61L 27/54* | (2006.01) | |
| *A61K 9/00* | (2006.01) | |

(52) U.S. Cl.
CPC ............ *A61L 27/34* (2013.01); *A61L 27/227* (2013.01); *A61L 27/52* (2013.01); *A61L 27/54* (2013.01); *A61K 9/0024* (2013.01); *A61L 2400/06* (2013.01); *A61L 2430/24* (2013.01); *A61L 2430/40* (2013.01)

(58) Field of Classification Search
None
See application file for complete search history.

(56) References Cited

U.S. PATENT DOCUMENTS

| | | | |
|---|---|---|---|
| 8,409,605 B2 | 4/2013 | Hnojewyj et al. | |
| 2008/0175817 A1* | 7/2008 | Hnojewyj ............... | C08L 89/00 424/93.1 |
| 2010/0322993 A1 | 12/2010 | Mollenhauer et al. | |
| 2012/0258147 A1 | 10/2012 | Mollenhauer et al. | |
| 2019/0192733 A1 | 6/2019 | Wurst et al. | |

OTHER PUBLICATIONS

Gao et al. "Thiolated human serum albumin cross-linked dextran hydrogels as macroscale delivery system", Soft Matter, 10, 4869-4874 (Year: 2014).*

* cited by examiner

*Primary Examiner* — Isis A Ghali
(74) *Attorney, Agent, or Firm* — Lewis Kohn & Walker LLP; David M. Kohn (57) ABSTRACT

A cell-free combination for use in the controlled, especially decelerated or retarded, release of active ingredient and/or in the production of a formulation in hydrogel form, especially depot formulation in hydrogel form, and/or as a formulation in hydrogel form, especially depot formulation in hydrogel form, and/or for the coating of a medical product, especially implant, preferably with a formulation in hydrogel form, especially depot formulation in hydrogel form, wherein the cell-free combination comprises a first component and a second component, the first component comprising cross-linkable albumin and the second component comprising a crosslinking agent for the albumin. Additionally, a hydrogel-forming material or hydrogel, to a kit or multicomponent system, to a medical product or a pharmaceutical formulation, to a discharge device, and to uses of the cell-free combination and of the hydrogel-forming material or hydrogel.

22 Claims, 1 Drawing Sheet

CELL-FREE COMBINATION, HYDROGEL-LIKE MATERIAL OR HYDROGEL AND USE OF SAME

FIELD OF APPLICATION AND PRIOR ART

The present invention relates to a cell-free combination, to a hydrogel-forming material or hydrogel, to a kit, to a medical product or a pharmaceutical formulation, to a discharge device, and also to uses of the cell-free combination and of the hydrogel-forming material or hydrogel.

It is known practice to administer active ingredients by way of a suitable vector. Known examples include the use of hormone patches, analgesic patches furnished with opioids, hormone-laden polymeric implants, and also creams and ointments which have been provided with hormones and/or with nonsteroidal anti-inflammatories. A disadvantage here, however, is the risk of detachments of active ingredient. In the case of hormone patches or analgesic patches, for example, perspiration, movement or showering may result in losses of active ingredient. Depending on the active ingredient, this may be accompanied by instances of skin irritation. In any case, premature detachments of active ingredient entail the risk of an overly low level of active ingredient at the desired site of action.

Generally speaking, active ingredients are administered orally or parenterally and develop their effect by reaching an effective concentration at the desired site of action in the body of a patient. In order to maintain the active ingredient level, regular repeat doses are necessary, often daily or even several times daily.

One problematic issue may be the incidence of unwanted systemic effects (side effects), since often it is necessary for more or less the entire body of a patient to be flooded with an active ingredient in order to achieve even a sufficient level of active ingredient at a site of action, which is often only locally defined.

A further problem may lie in a systemic disadvantaging of the desired site of action. Such disadvantaging may even result in active ingredient concentrations at the site of action being lower than at other sites/compartments of a patient's body which are not a target for the treatment.

Even locally administered active ingredients often remain at the desired site of action for too short a time, and may enter into the rest of a patient's body at relevant active ingredient levels.

The disadvantages described above are particularly problematic in the case of comorbidities and in extremis may mean that an inherently necessary therapy with an active ingredient intended for local effect cannot be carried out because of contraindications arising from the systemic distribution and the effect of said ingredient.

In the case of oral administration, a further problem is frequently that of a fluctuating or insufficient level of active ingredient. Fluctuating or insufficient supply of active ingredient may result from the interruptions naturally associated with oral administration, such as nighttime, or from a lack of patient compliance, from individual forgetfulness or other patient-specific factors, such as disorders of absorption and/or digestion, for example.

It is also known practice to provide active ingredients as formulations in hydrogel form, especially depot formulations in hydrogel form. The use of hydrogels is appropriate because of their particular properties, such as, for example, their high water content, their elasticity, their flexibility, and their biocompatibility. Many hydrogels are formed only after administration, in situ. Examples of such hydrogels are based on poloxamers and are available commercially under the names Synperonics, Pluronics, and Kolliphor. These hydrogels consist of nonionic triblock copolymers and are composed of a central hydrophobic chain of polypropylene oxide, which is flanked by two hydrophilic polyethylene oxide chains.

One depot formulation is available commercially under the name MedinGel™ (BEPO™). This formulation consists of a biodegradable, monodisperse, three-dimensional network of hydrophilic polyethylene glycol chains, crosslinked with hydrophobic polylactic acid chains. In an aqueous medium, semisolid microdomains are formed, into which various active ingredients can be introduced.

Another depot formulation is the Gamma or LiQuid Polymer (LQP) technology from InGell Labs (Groningen, The Netherlands). The formulation is based on copolymers which comprise caprolactone- and also lactide-PEG block units, with the formulation forming a flexible and biocompatible depot for active ingredients. The technology releases an active ingredient over a period ranging from days to weeks, and is based on the formation of a thermoreversible hydrogel having a polymer fraction of 15% to 20%. The remainder of the hydrogel consists of water and active ingredient.

A further depot formulation, the stabilized injectable formulation (SIF) from Foresee Pharmaceuticals Inc. (Newark, USA), is currently undergoing clinical evaluation. The SIF technology is based on biodegradable materials in biocompatible solvents. The system is made available in ready-to-use syringes and forms a depot in situ. The active ingredient can be controlledly released over a period ranging from days to months, by diffusion and biodegradation of the depot matrix.

A disadvantage with conventional depot formulations is that they provide only a partial solution to the problems described at the outset. Even repeat administrations often lead to an uneven profile in the level of active ingredient, and are comparatively burdensome or complicated.

Another disadvantage is that many polymer-based or implant-based formulations require a large number of production steps, usually using organic solvents. The compatibility of these with the active ingredient is often hard to predict and in general compromises the stability or activity of an active ingredient.

BRIEF DESCRIPTION OF THE DRAWINGS

The novel features of the present invention are set forth herein embodied in the form of the claims of the invention. Features and advantages of the present invention may be best understood by reference to the following detailed description of the invention, setting forth illustrative embodiments and preferred features of the invention, as well as the accompanying drawings, of which:

PROBLEM AND SOLUTION

The problem addressed by the present invention is therefore that of providing a product which at least partially avoids the disadvantages described at the outset, and in particular is in a position to enable preferably continuous release of active ingredient and/or increased active ingredient residence time and/or elevated concentration of active ingredient at a site of action. Furthermore, the product is preferably to be distinguished by a certain compatibility with active ingredient.

This problem is solved in accordance with the invention by means of a cell-free combination as per independent claim 1, by a hydrogel-forming material or hydrogel as per claim 19, by a kit as per claim 20, by a medical product or a pharmaceutical formulation as per claim 21, and by uses as per claims 23 and 24. Preferred embodiments of the invention are defined in the dependent claims. The wording of all of the claims is hereby made part of the content of the present description through express reference.

Further subject matter solving the problem addressed by the invention is disclosed in the description.

According to a first aspect, the invention relates to a cell-free combination, preferably for use in the controlled, especially decelerated and/or retarded, release of active ingredient
and/or
in the production of a formulation in hydrogel form, especially depot formulation in hydrogel form,
and/or
as a formulation in hydrogel form, especially depot formulation in hydrogel form,
and/or
for the coating of a medical product, especially implant, preferably with a formulation in hydrogel form, especially depot formulation in hydrogel form.

A particular feature of the cell-free combination is that it comprises a first component and a second component, the first component comprising crosslinkable albumin and the second component comprising a crosslinking agent, especially a biocompatible crosslinking agent, for the albumin.

The expression "cell-free combination" is intended in the sense of the present invention to refer to a combination which is free from cells, especially free from tissue cells and/or stem cells.

The expression "combination" is intended in the sense of the present invention to refer to a product, especially in the form of a kit, a multicomponent system or a hydrogel-forming material or hydrogel, that comprises at least two different components, it being possible for the components to be spatially separate from one another or to have been mixed with one another. Through mixing of the components it is possible with preference to produce a hydrogel-forming material or a hydrogel, with the production of the hydrogel-forming material or hydrogel being based preferably on a crosslinking process.

The expression "crosslinkable albumin" is intended in the sense of the present invention to refer to an albumin which by virtue of its chemical nature, especially by virtue of a suitable functionalization, can be crosslinked with the aid of a crosslinking agent. This crosslinking may be based in particular on the formation of ionic bonds and/or hydrogen bonds and/or hydrophobic interactions and/or covalent bonds between the albumin and the crosslinking agent. The crosslinking of the albumin is based preferably on the formation of covalent bonds between the albumin and the crosslinking agent. With particular preference the crosslinking of the albumin is based on a Michael addition between electrophilic groups, preferably thiol-reactive groups, of the albumin and nucleophilic groups, especially thiol and/or thiolate groups, of the crosslinking agent.

The expression "crosslinking agent for the albumin" is intended in the sense of the present invention to refer to a crosslinking agent which by virtue of its chemical nature, especially by virtue of a suitable functionalization, is capable of crosslinking the crosslinkable albumin. The crosslinking, as mentioned in the preceding paragraph, may be based especially on the formation of ionic bonds and/or hydrogen bonds and/or hydrophobic interactions and/or covalent bonds between the albumin and the crosslinking agent. The crosslinking of the albumin is based preferably on the formation of covalent bonds between the albumin and the crosslinking agent. With particular preference the crosslinking of the albumin is based on a Michael addition between electrophilic groups, preferably thiol-reactive groups, of the albumin and nucleophilic groups, especially thiol and/or thiolate groups, of the crosslinking agent.

The expression "Michael acceptor groups" is intended in the sense of the present invention to refer to electrophilic groups which are capable of entering with nucleophilic groups (Michael donor groups) into a Michael addition.

The expression "Michael donor groups" is intended in the sense of the present invention to refer to nucleophilic groups which are capable of entering with electrophilic groups (Michael acceptor groups) into a Michael addition.

The expression "thiol-reactive groups" is intended in the sense of the present invention to refer to functional groups which are capable of reacting with thiol and/or thiolate groups, preferably so as to form covalent bonds and/or linkages.

The expression "functionalization" or "functionalized" or "functionalize" is intended in the sense of the present invention, in the context of the crosslinkable albumin, to refer to any—concluded—process by which the albumin is endowed, through modification with groups or addition of groups, for example, with a function that the albumin does not normally possess. With regard to suitable groups, reference may be made to the groups that are mentioned below in relation to functionalization of the albumin, such as especially maleimide groups.

The expression "degree of functionalization" is intended in the sense of the present invention, in the context of the crosslinkable albumin, to refer to the number of groups, especially electrophilic groups, preferably Michael acceptor groups such as especially maleimide groups, per individual albumin molecule.

The expression "thiol-functionalized" is intended in the sense of the present invention, in the context of the crosslinking agent, to refer to a crosslinking agent which comprises thiol groups (SH groups) or is provided with thiol groups.

The expression "thiol-functionalized" is intended in the sense of the present invention, in the context of the crosslinking agent, to refer to a crosslinking agent which comprises thiolate groups ($S^-$ groups) or is provided with thiolate groups.

The expression "degree of functionalization" is intended in the sense of the present invention, in the context of the crosslinking agent, to refer to the number of groups, especially nucleophilic groups, preferably Michael donor groups such as especially thiol groups and/or thiolate groups, per individual crosslinking agent molecule. In the case of a polymeric crosslinking agent wherein nonterminal monomer units (and optionally terminal monomer units as well) are functionalized, the expression "degree of functionalization" in the sense of the present invention means preferably the number of groups, especially nucleophilic groups, preferably Michael donor groups such as especially thiol groups and/or thiolate groups, per 100 monomer units of the polymeric crosslinking agent.

The expression "formulation" is intended in the sense of the present invention to refer to an administration form or preparation, especially in the form of a hydrogel-forming material or a hydrogel, which comprises an active ingredient, preferably an active pharmaceutical ingredient (medicament).

The expression "pharmaceutical formulation" is intended in the sense of the present invention to refer to an administration form or preparation, especially in the form of a hydrogel-forming material or a hydrogel, which comprises an active pharmaceutical ingredient (medicament).

The expression "depot formulation" is intended in the sense of the present invention to refer to a formulation which is capable of releasing an active ingredient over a relatively long period, as for example over a period of several days, weeks or months.

The expression "active ingredient" is intended in the sense of the present invention to designate a substance which in an organism has a specific action and/or evokes a specific response.

The expression "active pharmaceutical ingredient" is intended in the sense of the present invention to refer to a substance which possesses a curative effect, i.e., acts as a medicament.

The expression "biopharmaceutical" is intended in the sense of the present invention to refer to a medicament which has been produced by biotechnology or using genetically modified organisms.

The expression "biopolymer" is intended in the sense of the present invention to refer to a polymer which occurs in nature or whose structure matches that of a polymer which occurs in nature.

The expression "hydrogel-forming material" is intended in the sense of the present invention to refer to a material which is produced or producible by crosslinking of the albumin with the crosslinking agent and which together with water or an aqueous fluid forms a hydrogel.

The expression "hydrogel" is intended in the sense of the present invention to refer to a water-containing polymer network which comprises a hydrogel-forming material, preferably albumin crosslinked with crosslinking agent, and water.

The expression "medical product" is intended in the sense of the present invention to refer to an article or substance which is used for human medical therapy or diagnostics, where the intended principal effect, in contrast to medicinal products, is primarily not pharmacological, metabolic or immunological, but instead usually physical or physicochemical.

Entirely surprisingly it has emerged that a cell-free combination according to the present invention, and especially a hydrogel-forming material or hydrogel according to the present invention, produced or producible by mixing of the components of the cell-free combination, can be used preferably as a depot matrix or depot formulation, for the controlled release of active ingredients, especially over a number of days, without adversely affecting the structure and/or the function of the active ingredients. In this way it is possible advantageously to achieve especially an interruption-free level of action in vivo.

It has emerged, furthermore, that a cell-free combination according to the present invention, and especially a hydrogel-forming material or hydrogel according to the present invention, produced or producible by mixing of the components of the cell-free combination, can be used preferably as a depot matrix or depot formulation, for the even or homogeneous release of active ingredients, especially over a number of days. In this way it is possible with particular advantage to achieve an even or especially constant level of action in vivo.

It has emerged, furthermore, that the production of a hydrogel-forming material or a hydrogel according to the present invention, by mixing of the components of the cell-free combination, does not exert any deleterious effect on the structure and/or activity of active ingredients which may be present in the first component and/or second component.

With particular advantage, especially by modifying the degree of functionalization of the crosslinkable albumin and/or of the crosslinking agent and/or by modifying the crosslinkable albumin fraction in the first component and/or the crosslinking agent fraction in the second component, it is possible in a targeted way to exert deliberate control over the structure, especially the degree of crosslinking and/or the gel strength, of a hydrogel-forming material or hydrogel produced or producible by mixing of the components of the cell-free combination, and hence over the rate or velocity of release of active ingredients from such a material or hydrogel. Consequently, it is especially possible to exert a targeted influence over, and especially to increase, the residence time and/or the concentration of active ingredients, for example, at a desired local site of action. In the case of an intended systemic effect, it is possible, via influencing the rate of release, for any unwanted side effects to be either entirely avoided or else at least reduced.

The findings described above had been successfully verified by means of release studies using therapeutic antibodies as active ingredients; this will be addressed in more detail in the Examples section.

In an embodiment of the invention, the cell-free combination is adapted for subcutaneous administration, preferably subcutaneous injection. In other words, according to one embodiment of the invention, the cell-free combination is used for subcutaneous administration, preferably subcutaneous injection. By subcutaneous administration, it is possible, via an active ingredient which may be present in the first component and/or second component of the cell-free combination, with particular advantage to achieve a local and/or systemic level of active ingredient. Accordingly, through subcutaneous administration of the cell-free combination extremely close to a local site of action, an exclusively or almost exclusively locally resident level of action can be achieved. Alternatively, by diffusion of the active ingredient into vascular pathways of a human body, especially into blood vessels and/or lymph vessels, it is possible to achieve a systemic effect.

In a further embodiment of the invention, the cell-free combination is adapted for surgical, especially minimally invasive, administration, preferably injection, especially for administration, preferably injection, into a tissue cavity, preferably into a tissue cavity resulting from tumor removal, or into a joint, preferably knee joint. In other words, the cell-free combination, according to a further embodiment of the invention, is used for surgical, especially minimally invasive, administration, preferably injection, especially for administration, preferably injection, into a tissue cavity, preferably into a tissue cavity resulting from tumor removal, or into a joint, preferably knee joint.

In a further embodiment of the invention, the cell-free combination is adapted for facet joint infiltration. In other words, according to a further embodiment of the invention, the cell-free combination is used for facet joint infiltration.

The crosslinkable albumin is preferably crosslinkable human albumin, especially crosslinkable human serum albumin. This contributes with particular advantage to a further increase in the active ingredient compatibility of the cell-free combination and also, especially, of a hydrogel-forming material or hydrogel produced or producible by mixing of the first component and second component of the cell-free combination.

In principle, the crosslinkable albumin, however, may also be of xenogeneic origin, especially bovine, porcine or equine origin.

In a further embodiment of the invention, the albumin is a functionalized albumin.

In a further embodiment of the invention, the albumin is functionalized by groups, especially electrophilic groups, preferably Michael acceptor groups, more preferably thiol-reactive groups. The groups are preferably selected from the group consisting of maleimide groups, vinyl sulfone groups, acrylate groups, alkyl halide groups, azirine groups, pyridyl groups, thionitrobenzoic acid groups, arylating groups, and combinations of at least two of the stated groups.

With particular preference the crosslinkable albumin is functionalized with maleimide groups. In other words it is particularly preferred in accordance with the invention if the crosslinkable albumin is maleimide-functionalized albumin, especially maleimide-functionalized serum albumin. It is especially preferred if the crosslinkable albumin is maleimide-functionalized albumin, especially maleimide-functionalized serum albumin, of human origin. By functionalization with maleimide groups it is possible to enable particularly effective crosslinking of the albumin and hence a particularly controllable release of active ingredients which may be present in the first component and/or in the second component of the cell-free combination.

In a further embodiment of the invention, the crosslinkable albumin has a degree of functionalization of 2 groups to 60 groups, especially 3 groups to 45 groups, preferably 5 groups to 35 groups, per albumin molecule. With regard to suitable groups, reference may be made to the groups stated in the preceding paragraph. The groups are preferably maleimide groups. Via the degree of functionalization of the crosslinkable albumin it is possible in a particularly advantageous way to control the release of active ingredients from the cell-free combination, especially from a hydrogel-forming material or hydrogel produced or producible by mixing of the first component and the second component of the cell-free combination. Hence a higher degree of functionalization of the albumin promotes with particular advantage a greater crosslinking of the albumin and especially the formation of a higher degree of crosslinking of the cell-free combination, especially of a hydrogel-forming material or hydrogel produced or producible by mixing of the first component and the second component of the cell-free combination. In this way it is possible to achieve decelerated or retarded release of active ingredients which may be present in the first component and/or second component of the cell-free combination. This in turn with particular advantage promotes the formation of a longer and especially more uniform level of active ingredient at a desired site of action. Furthermore, a lower release of active ingredient promotes the occurrence of a lower level of active ingredient, thereby making it possible to prevent or else at least reduce contraindications deriving from systemic effects. The advantages described in this paragraph may alternatively also be realized through a lower degree of functionalization of the albumin for a given number of groups such as especially maleimide groups and a higher number of crosslinkable albumin molecules.

In a further embodiment of the invention, the crosslinkable albumin has a fraction of 0.1 wt % to 11 wt %, based on the total volume of the cell-free combination, preferably based on the total volume of a cell-free combination which is present in the form of a hydrogel-forming material or hydrogel. The albumin fraction of the cell-free combination represents a further parameter with which it is possible advantageously to influence the release of active ingredients which may be present in the first component and/or second component of the cell-free combination. For instance, a higher albumin fraction may likewise promote greater crosslinking of the albumin and especially the formation of a higher degree of crosslinking of the cell-free combination, especially of a hydrogel-forming material or hydrogel produced or producible by mixing of the first component and second component of the cell-free combination. As a result it is possible to achieve decelerated or retarded release of active ingredients which may be present in the first component and/or second component of the cell-free combination. This in turn advantageously promotes the formation of a longer and especially more uniform level of active ingredient at a desired site of action. Furthermore, a lower release of active ingredient promotes the occurrence of a lower active ingredient level, thereby making it possible to prevent or else at least reduce unwanted systemic effects.

Furthermore, interactions of active ingredients which may be present in the first component and/or second component of the cell-free combination with the albumin, especially similarly to a plasma protein binding, represent a factor which can influence the release of active ingredients, and so with increasing albumin fraction it is also possible to achieve increasing control, especially deceleration or retardation, of release of an active ingredient.

In a further embodiment of the invention, the crosslinking agent has nucleophilic groups, especially Michael donor groups, preferably thiol groups (SH groups) and/or thiolate groups (S⁻ groups).

The crosslinking agent preferably has a degree of functionalization of at least 2, especially 2, 3 or four. A polymeric crosslinking agent wherein nonterminal (and, optionally, terminal monomer) units are functionalized may have, for example, a degree of functionalization of 1% to 25%, based on 100 monomer units of the polymeric crosslinking agent. Regarding suitable polymeric crosslinking agents, reference may be made to the statements below, particularly to the thiol-functionalized polymers disclosed below. The degree of functionalization of the crosslinking agent represents a further parameter for influencing the release of active ingredients which may be present in the first component and/or second component of the cell-free combination.

The crosslinking agent may further be a linear, i.e., unbranched, crosslinking agent. With particular advantage the molecular length of the crosslinking agent as well represents a parameter by which it is possible to control the release of active ingredients which may be present in the first component and/or second component of the cell-free combination. Thus relatively long-chain crosslinking agents may contribute to the formation of structures, especially in the form of a hydrogel-forming material or hydrogel, having relatively large interstices, thus allowing active ingredients which may be present in the first component and/or second component of the cell-free combination to be released more quickly and especially over a shorter time. Conversely, relatively short-chain crosslinking agents may contribute to a slower release of active ingredient.

The crosslinking agent may especially be a linear crosslinking agent having two terminal nucleophilic groups, especially Michael donor groups, preferably thiol groups (SH groups) and/or thiolate groups (S⁻ groups), per crosslinking agent molecule.

Furthermore, the crosslinking agent may be a branched, especially multiarm, as for example three- or four-arm, crosslinking agent. By using a branched crosslinking agent it is possible with particular advantage to achieve greater crosslinking of the albumin and particularly the formation of a relatively high degree of crosslinking of the cell-free combination, especially of a hydrogel-forming material or hydrogel produced or producible by mixing of the first component and second component of the cell-free combination.

The crosslinking agent may especially be a three-arm crosslinking agent having three terminal nucleophilic groups, especially Michael donor groups, preferably thiol groups (SH groups) and/or thiolate groups (S⁻ groups), per crosslinking agent molecule, or may be a four-arm crosslinking agent having four terminal nucleophilic groups, especially Michael donor groups, preferably thiol groups (SH groups) and/or thiolate groups (S⁻ groups), per crosslinking agent molecule.

The crosslinking agent may further and in particular be a thiol-functionalized and/or thiolate-functionalized polymer, especially biopolymer, preferably polysaccharide such as mucopolysaccharide. With regard to suitable polymers, reference is made to the polymers disclosed in the following paragraph.

The crosslinking agent is preferably selected from the group consisting of thiol-functionalized and/or thiolate-functionalized (i.e., SH-functionalized and/or S⁻-functionalized) polyethylene glycol such as dithio-polyethylene glycol or bis-thio-polyethylene glycol (dithio-PEG or bis-thio-PEG), thiol-functionalized and/or thiolate-functionalized (i.e., SH-functionalized and/or S⁻-functionalized) hyaluronic acid, thiol-functionalized and/or thiolate-functionalized (i.e., SH-functionalized and/or S⁻-functionalized) starch, thiol-functionalized and/or thiolate-functionalized (i.e., SH-functionalized and/or S⁻-functionalized) dextran, thiol-functionalized and/or thiolate-functionalized (i.e., SH-functionalized and/or S⁻-functionalized) polyvinyl alcohol, thiol-functionalized and/or thiolate-functionalized (i.e., SH-functionalized and/or S⁻-functionalized) polyvinylpyrrolidone, and mixtures of at least two of the stated crosslinking agents.

With particular preference the crosslinking agent is dithio-polyethylene glycol or bis-thio-polyethylene glycol (dithio-PEG or bis-thio-PEG). The dithio-polyethylene glycol may especially have a molecular weight of 1000 Da to 20 000 Da.

The crosslinking agent, furthermore, may be a thiol-functionalized polyethylene glycol having three terminal thiol groups, i.e., a three-arm, thiol-functionalized polyethylene glycol having a degree of functionalization of 3. The thiol-functionalized polyethylene glycol preferably possesses a molecular weight of 1000 Da to 30 000 Da.

The crosslinking agent, furthermore, may be a thiol-functionalized polyethylene glycol having four terminal thiol groups, i.e., a four-arm, thiol-functionalized polyethylene glycol having a degree of functionalization of 4. The thiol-functionalized polyethylene glycol preferably possesses a molecular weight of 1000 Da to 40 000 Da.

Furthermore, the crosslinking agent may especially be a thiol-functionalized hyaluronic acid having a molecular weight of 5000 Da to 100 000 Da. In relation to the thiol groups, the hyaluronic acid preferably has a degree of functionalization of 1% to 25%, based on 100 monomer units of the hyaluronic acid.

In a further embodiment of the invention, the crosslinking agent has a fraction of 0.1 wt % to 30 wt %, based on the total volume of the cell-free combination, preferably based on the total volume of a cell-free combination in the form of a hydrogel-forming material or hydrogel. The crosslinking agent fraction of the cell-free combination constitutes a further parameter permitting deliberate control, advantageously, over the release of active ingredients which may be present in the first component and/or second component of the cell-free combination. Through a higher crosslinking agent fraction, then, it is likewise possible to achieve greater crosslinking of the albumin and especially the formation of a higher degree of crosslinking of the cell-free combination, especially of a hydrogel-forming material or hydrogel produced or producible by mixing of the first component and second component of the cell-free combination, and hence a slower release of active ingredient. This in turn with particular advantage favors the formation of a longer and especially more uniform level of active ingredient at a desired site of action. Furthermore, a lower release of active ingredient promotes the occurrence of a lower active ingredient level, so making it possible to prevent or else at least reduce side effects.

In a further embodiment of the invention, the first component, especially only the first component, further comprises an active ingredient.

The first component may for example have a fraction of the active ingredient of 0.1 wt % to 25 wt %, based on the total weight of the first component, especially of a first component present in aqueous form.

In a further embodiment of the invention, the second component, especially only the second component, further comprises an active ingredient.

The second component may for example have a fraction of the active ingredient of 0.1 wt % to 25 wt %, based on the total weight of the second component, especially of a second component present in aqueous form.

In a further embodiment of the invention, the first component and the second component of the cell-free combination each comprise an active ingredient.

In a further embodiment of the invention, the active ingredient is a low molecular mass compound, i.e., a compound having a molecular mass ≤800 g/mol. Regarding suitable low molecular mass compounds, reference may be made to the low molecular mass compounds disclosed below in the context of the active ingredient.

In a further embodiment of the invention, the active ingredient is a high molecular mass compound or a polymer, especially biopolymer. With regard to suitable polymers, especially biopolymers, reference may be made to the polymers disclosed below in the context of the active ingredient.

In a further embodiment of the invention, the active ingredient is a natural substance, i.e., a substance produced by living organisms such as plants, animals or microorganisms.

In a further embodiment of the invention, the active ingredient is a synthetically produced active ingredient.

In a further embodiment of the invention, the active ingredient is an active pharmaceutical ingredient (medicament), especially a biopharmaceutical (biological).

In a further embodiment of the invention, the active ingredient is selected from the group consisting of peptide (such as oligopeptide), protein, therapeutic protein, antibody or antibody fragment, immunosuppressant, cytokine, growth factor, chemokine, differentiation factor, modulation factor, immunostimulant, hormone (such as steroid hormone and/or metabolic hormone), cytostatic agent or chemotherapeutic agent, antiinflammatory, analgesic, chondroprotective agent, antibiotic, polysaccharide, lipid, DNA, RNA, siRNA, agent for gene therapy, vitamin, and mixtures of at least two of the stated active ingredients.

In a further embodiment of the invention, the active ingredient is an antibody, especially a therapeutic antibody, or an antibody fragment, especially a therapeutic antibody fragment. The antibody may be a monoclonal antibody or a polyclonal antibody. The antibody fragment may especially be a Fab fragment (antigen-binding fragment) or a single-domain antibody (nanoantibody).

The antibody or the antibody fragment is preferably selected from the group consisting of alemtuzumab, apolizumab, atezolizumab, avelumab, bevacizumab, blinatumomab, catumaxomab, cetuximab, daratumumab, durvalumab, eculizumab, elotuzumab, emicizumab, epratuzumab, gemtuzumab, gemtuzumab ozogamicin, ibritumomab tiuxetan, inotuzumab ozogamicin, ipilimumab, mogamulizumab, necitumumab, nivolumab, obinutuzumab, ofatumumab, olaratumab, oregovomab, panitumumab, pembrolizumab, pertuzumab, ramucirumab, rituximab, rovalpituzumab tesirin, siltuximab, tremelimumab, tositumomab, trastuzumab, zanolimumab, adalimumab, alefacept, anifrolumab, basiliximab, belimumab, brodalumab, canakinumab, certolizumab, clazakizumab, daclizumab, fasinumab, guselkumab, golimumab, infliximab, ixekizumab, mavrilimumab, muromonab-CD3, natalizumab, secukinumab, sifalimumab, sirukumab, tocilizumab, ustekinumab, vedolizumab, alirocumab, evolocumab, abciximab, bezlotoxumab, motavizumab, palivizumab, aducanumab, erenumab, ocrelizumab, solanezumab, ranibizumab, dupilumab, efalizumab, etanercept, nemolizumab, ustekinumab, tositumab, benralizumab, mepolizumab, omalizumab, reslizumab, tralokinumab, denosumab, romosozumab, fragments, especially Fab fragments, thereof, and mixtures of at least two of the stated antibodies or antibody fragments.

In a further embodiment of the invention, the active ingredient is an immunosuppressant which is preferably selected from the group consisting of glucocorticoids, cytostatics, antibodies, calcineurin inhibitors, TOR inhibitors, and mixtures of at least two of the stated immunosuppressants.

In a further embodiment of the invention, the active ingredient is a cytokine which is preferably selected from the group consisting of interleukins, interferons, tumor necrosis factors, colony-stimulating factors, and mixtures of at least two of the stated cytokines.

The interleukins may especially be selected from the group consisting of interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interleukin-13 (IL-13), interleukin-16 (IL-16), interleukin-18 (IL-18), interleukin-23 (IL-23), and mixtures of at least two of the stated interleukins.

Suitable interferons may be selected from the group consisting of IFN-α, IFN-β, IFN-γ, and mixtures of at least two of the stated interferons. The interferons may especially be selected from the group of IFN-α-2a, IFN-α-2b, IFN-β-1a, IFN-β-1b, and mixtures of at least two of the stated interferons.

The tumor necrosis factors may be selected from the group consisting of TNF-α, TNF-β, and mixtures thereof.

The colony-stimulating factors may be selected from the group consisting of erythropoietin (EPO), thrombopoietin (TPO), granulocyte-colony-stimulating factor (G-CSF), granulocyte-macrophage-colony-stimulating factor (GM-CSF), macrophage-colony-stimulating factor (M-CSF), and mixtures of at least two of the stated colony-stimulating factors.

In a further embodiment of the invention, the active ingredient is a hormone, especially steroid hormone, which is preferably selected from the group consisting of cortisol, corticosterone, sex hormone, (synthetic or semisynthetic) derivatives thereof, and mixtures of at least two of the stated hormones. The sex hormone may especially be selected from the group consisting of testosterone, estrogen, progesterone, (synthetic or semisynthetic) derivatives thereof, and mixtures of at least two of the stated sex hormones.

In a further embodiment of the invention, the active ingredient may be a vitamin, especially vitamin D and/or a derivative thereof.

In a further embodiment of the invention, the active ingredient is a cytostatic or chemotherapeutic agent which is preferably selected from the group consisting of cyclophosphamide, methotrexate, azathioprine, mitoxantrone, mycophenolate mofetil, and mixtures of at least two of the stated cytostatics or chemotherapeutic agents.

In a further embodiment of the invention, the active ingredient is an antiinflammatory, especially a steroidal antiinflammatory and/or nonsteroidal anti-inflammatory. The antiinflammatory is preferably selected from the group consisting of triamcinolone, triam acetonide, betametasone, dexametasone, ibuprofen, flurbiprofen, naproxen, ketoprofen, tiaprofenic acid, diclofenac, indometacin, flufenanimic acid, mefenamic acid, piroxicam, tenoxicam, meloxicam, lornoxicam, parecoxib, etoricoxib, celecoxib, esters thereof, salts thereof, suspensions, especially crystal suspensions, thereof, and mixtures of at least two of the stated antiinflammatories.

In a further embodiment of the invention, the active ingredient is an analgesic which is preferably selected from the group consisting of morphine, fentanyl, methadone, oxycodone, epibatidine, scopolamine, acetylsalicylic acid, methyl salicylate, diflunisal, diclofenac, meloxicam, piroxicam, paracetamol, metamizole, phenazone, ziconotide, flupirtin, ketamine, tetrahydrocannabinol, cannabidiol, and mixtures of at least two of the stated analgesics.

In a further embodiment of the invention, the active ingredient is a chondroprotective agent which is preferably selected from the group consisting of hyaluronic acid, chrondroitin sulfate, glucosamine sulfate, oxaceprol, antioxidants such as vitamin E, ademethionine (S-adenosylmethionine SAM), and mixtures of at least two of the stated chondroprotective agents.

In a further embodiment of the invention, the active ingredient is an antibiotic which is preferably selected from the group consisting of beta-lactams, glycopeptides, polyketides, aminoglycoside antibiotics, polypeptide antibiotics, quinolones, sulfonamides, and mixtures of at least two of the stated antibiotics.

The beta-lactam antibiotics, for example, may be selected from the group consisting of penicillins, cephalosporins, monobactams, carbapenems, and mixtures of at least two of the stated beta-lactam antibiotics.

The glycopeptides may be selected, for example, from the group consisting of vancomycin, dalbavancin, teicoplanin, and mixtures of at least two of the stated glycopeptides.

The polyketides may be selected, for example, from the group consisting of tetracyclines, macrolide antibiotics such as erythromycin, and mixtures of at least two of the stated polyketides.

The polypeptide antibiotics may be selected, for example, from the group consisting of polymyxins, bacitracin, tyrothricin, and mixtures of at least two of the stated antibiotics.

In a further embodiment of the invention, the first component, especially only the first component, further comprises salts and/or amino acids and/or sugar alcohols and/or saccharides. The salts may especially be sodium chloride and/or buffer salts, preferably a phosphate buffer salt, especially a mixture of sodium dihydrogenphosphate and disodium hydrogenphosphate, and/or a potassium phosphate salt, especially a mixture of potassium dihydrogenphosphate and dipotassium hydrogenphosphate. An example of a suitable sugar alcohol is mannitol. The saccharides may be selected from the group consisting of sucrose, trehalose, cyclodextrins, and mixtures thereof.

In a further embodiment of the invention, the second component, especially only the second component, further comprises salts and/or amino acids and/or sugar alcohols and/or saccharides. The salts may especially be sodium chloride and/or buffer salts, preferably a phosphate buffer salt, especially a mixture of sodium dihydrogenphosphate and disodium hydrogenphosphate, and/or a potassium phosphate salt, especially a mixture of potassium dihydrogenphosphate and dipotassium hydrogenphosphate. An example of a suitable sugar alcohol is mannitol. The saccharides may be selected from the group consisting of sucrose, trehalose, cyclodextrins, and mixtures thereof.

In a further embodiment of the invention, the first component and the second component further comprise salts and/or amino acids and/or sugar alcohols and/or saccharides. Regarding suitable salts and/or amino acids and/or sugar alcohols and/or saccharides, reference is made to the statements given in the preceding paragraphs.

In a further embodiment of the invention, the first component and the second component are in a ratio, especially mixing ratio, of first component to second component of 10:1 to 1:1, as for example 4:1.

In a further embodiment of the invention, the first component, especially only the first component, is in aqueous form, preferably in the form of an aqueous solution. The aqueous form, especially aqueous solution, is preferably free from organic solvents. This allows an additional increase in the active ingredient compatibility of the cell-free combination, and especially of a hydrogel-forming material or hydrogel produced or producible by mixing of the components of the cell-free combination.

In a further embodiment of the invention, the second component, especially only the second component, is in aqueous form, preferably in the form of an aqueous solution. The aqueous form, especially aqueous solution, is preferably free from organic solvents. This allows an additional increase in the active ingredient compatibility of the cell-free combination, and especially of a hydrogel-forming material or hydrogel produced or producible by mixing of the components of the cell-free combination.

In a further embodiment of the invention, the first component and the second component are each in aqueous form, preferably in the form of an aqueous solution. The aqueous form, especially aqueous solution, is preferably free from organic solvents. This allows a particular increase in the active ingredient compatibility of the cell-free combination, and especially of a hydrogel-forming material or hydrogel produced or producible by mixing of the components of the cell-free combination.

In a further embodiment of the invention, the first component, especially only the first component, is in the form of a solid, especially in the form of a lyophilized solid.

In a further embodiment of the invention, the second component, especially only the second component, is in the form of a solid, especially in the form of a lyophilized solid.

In a further embodiment of the invention, the first component and the second component are each in the form of a solid, especially in the form of a lyophilized solid.

In a further embodiment of the invention, the first component is in the form of a solid, especially in the form of a lyophilized solid, and the second component is in aqueous form, preferably in the form of an aqueous solution. The aqueous form, especially aqueous solution, is preferably free from organic solvents.

In a further embodiment of the invention, the first component is in aqueous form, preferably in the form of an aqueous solution, and the second component is in the form of a solid, especially in the form of a lyophilized solid. The aqueous form, especially aqueous solution, is preferably free from organic solvents.

In a further embodiment of the invention, the first component and the second component are spatially separate from one another. In this embodiment of the invention, the cell-free combination is configured preferably as a kit or multicomponent system, especially two-component system. Usefully for this purpose the first component and the second component are accommodated in separate containers. The kit or multicomponent system may especially be a medical kit or a medical multicomponent system, especially two-component system, or a pharmaceutical kit or pharmaceutical multicomponent system, especially two-component system.

In a further embodiment of the invention, the first component and the second component have been mixed with one another. The crosslinkable albumin in this case is at least partially crosslinked, especially only partially or completely crosslinked. In this embodiment of the invention, the cell-free combination is preferably present at least partially, especially only partially or completely, as a hydrogel-forming material or hydrogel, especially as a formulation in hydrogel form, preferably depot formulation in hydrogel form.

In a further embodiment of the invention, the cell-free combination is a medical product, especially implant, or is a pharmaceutical formulation, especially a pharmaceutical depot formulation.

According to a second aspect, the invention relates to a hydrogel-forming material or hydrogel, preferably for use
  in the controlled, especially decelerated and/or retarded, release of active ingredient
  and/or
  in the production of a formulation in hydrogel form, especially depot formulation in hydrogel form,
  and/or
  as a formulation in hydrogel form, especially depot formulation in hydrogel form,
  and/or
  for the coating of a medical product, especially implant, preferably with a formulation in hydrogel form, especially depot formulation in hydrogel form.

A particular feature of the hydrogel-forming material or hydrogel is that it comprises a cell-free combination according to the first aspect of the invention, or consists of a cell-free combination according to the first aspect of the invention, or is produced or producible by mixing of the first component and of the second component of the cell-free combination according to the first aspect of the invention.

In an embodiment of the invention, the hydrogel-forming material or hydrogel is adapted for subcutaneous administration, preferably subcutaneous injection. In other words, the cell-free combination according to one embodiment of the invention is used for subcutaneous administration, preferably subcutaneous injection.

In a further embodiment of the invention, the hydrogel-forming material or hydrogel is adapted for surgical, especially minimally invasive, administration, preferably injection, especially for administration, preferably injection, into a tissue cavity, preferably into a tissue cavity resulting from tumor removal, or into a joint, preferably knee joint. In other words, the hydrogel-forming material or hydrogel, according to a further embodiment of the invention, is used for surgical, especially minimally invasive, administration, preferably injection, especially for administration, preferably injection, into a tissue cavity, preferably into a tissue cavity resulting from tumor removal, or into a joint, preferably knee joint.

In a further embodiment of the invention, the hydrogel-forming material or hydrogel is adapted for facet joint infiltration. In other words, according to a further embodiment of the invention, the hydrogel-forming material or hydrogel is used for facet joint infiltration.

In a further embodiment of the invention, the hydrogel-forming material or hydrogel has a fraction of albumin, especially functionalized albumin, preferably maleimide-functionalized albumin, of 0.1 wt % to 11 wt %, based on the total volume of the hydrogel-forming material or hydrogel.

In a further embodiment of the invention, the hydrogel-forming material or hydrogel has a fraction of crosslinking agent of 0.1 wt % to 30 wt %, based on the total volume of the hydrogel-forming material or hydrogel.

In a further embodiment of the invention, the hydrogel-forming material or hydrogel has a degree of crosslinking of 1 mmol/l to 8 mmol/l of crosslinking bonds that have formed. The expression "crosslinking bonds" is intended in this context to refer to the bonds which develop in the course of crosslinking between functional groups, such as especially maleimide groups, of the albumin, and functional groups, such as especially thiol groups and/or thiolate groups, of the crosslinking agent.

With regard to further features and advantages of the hydrogel-forming material or hydrogel, reference is made completely, in order to avoid unnecessary repetition, to the statements made in the context of the first aspect of the invention. The statements made therein in relation to the cell-free combination, especially to the first component, to the crosslinkable albumin, to the second component, and to the crosslinking agent are also valid mutatis mutandis for the hydrogel-forming material or hydrogel in accordance with the second aspect of the invention.

According to a third aspect, the invention relates to a kit or multicomponent system, preferably for use
  in the controlled, especially decelerated and/or retarded, release of active ingredient
  and/or
  in the production of a formulation in hydrogel form, especially depot formulation in hydrogel form,
  and/or
  as a formulation in hydrogel form, especially depot formulation in hydrogel form,
  and/or
  for the coating of a medical product, especially implant, preferably with a formulation in hydrogel form, especially depot formulation in hydrogel form.

A particular feature of the kit or multicomponent system is that it comprises, spatially separate from one another, the first and the second components of a cell-free combination according to the first aspect of the invention. Usefully for this purpose the first component and the second component are accommodated in separate containers.

Alternatively a particular feature of the kit or multicomponent system is that it comprises a hydrogel-forming material or a hydrogel according to the second aspect of the invention.

The kit or multicomponent system may especially be a medical kit or medical multicomponent system, or a pharmaceutical kit or pharmaceutical multicomponent system.

The kit or the multicomponent system preferably further comprises a discharge device for the components of the cell-free combination or for the hydrogel-forming material or hydrogel. The discharge device may comprise a twin-chamber syringe or dual-chamber syringe (single-piston syringe with two compartments separated from one another via a liquid-permeable membrane or a liquid-permeable diaphragm) and especially a mixing facility. The mixing facility is preferably designed to bring about mixing, especially homogeneous mixing, of the first component and the second component of the cell-free combination. As a result it is possible with particular advantage to ensure that there is sufficient crosslinking of the albumin with the crosslinking agent as early as during discharge. The discharge device may further comprise a cannula, which may be in fluid-conducting communication with a discharge aperture of the discharge device, especially of the mixing facility.

Furthermore, the kit or multicomponent system may further comprise solvent, especially water or an aqueous salt solution, preferably an aqueous buffer salt solution. This is advantageous if the first component and/or second component of the cell-free combination are present as solids. In that case the solvent may be used to liquefy (reconstitute) the first component and/or second component.

The multicomponent system described in the context of the third aspect of the invention may especially be a two-component system.

With regard to further features and advantages of the kit or multicomponent system, reference is made completely, in order to avoid unnecessary repetition, to the statements made in the context of the first aspect of the invention and second aspect of the invention. The statements made therein in relation to the cell-free combination, especially to the first component, to the crosslinkable albumin, to the second component, and to the crosslinking agent, and also in relation to the hydrogel-forming material or hydrogel are also valid mutatis mutandis for the kit or multicomponent system in accordance with the third aspect of the invention.

According to a fourth aspect of the invention, the invention relates to a medical product or a pharmaceutical formulation, preferably for use
  in the controlled, especially decelerated and/or retarded, release of active ingredient
  and/or
  in the production of a formulation in hydrogel form, especially depot formulation in hydrogel form,
  and/or
  as a formulation in hydrogel form, especially depot formulation in hydrogel form,
  and/or
  for the coating of a medical product, especially implant, preferably with a formulation in hydrogel form, especially depot formulation in hydrogel form.

A particular feature of the medical product or the pharmaceutical formulation is that the medical product or the pharmaceutical formulation comprises a cell-free combination according to the first aspect of the invention, or consists of such a combination, or comprises a hydrogel-forming material or hydrogel according to the second aspect of the invention, or consists of such a hydrogel-forming material or hydrogel.

The medical product is preferably an implant.

The pharmaceutical formulation is preferably a depot formulation.

In an embodiment of the invention, the medical product or the pharmaceutical formulation is adapted for subcutaneous administration, preferably subcutaneous injection. In other words, the medical product or the pharmaceutical formulation according to one embodiment of the invention is used for subcutaneous administration, preferably subcutaneous injection.

In a further embodiment of the invention, the medical product or the pharmaceutical formulation is adapted for surgical, especially minimally invasive, administration, preferably injection, especially for administration, preferably injection, into a tissue cavity, preferably into a tissue cavity resulting from tumor removal, or into a joint, preferably knee joint. In other words, the medical product or the pharmaceutical formulation, according to a further embodiment of the invention, is used for surgical, especially minimally invasive, administration, preferably injection, especially for administration, preferably injection, into a tissue cavity, preferably into a tissue cavity resulting from tumor removal, or into a joint, preferably knee joint.

In a further embodiment of the invention, the medical product or the pharmaceutical formulation is adapted for facet joint infiltration. In other words, according to a further embodiment of the invention, the medical product or the pharmaceutical formulation is used for facet joint infiltration.

The medical product may especially be an implant.

With regard to further features and advantages of the medical product or the pharmaceutical formulation, reference is made completely, in order to avoid unnecessary repetition, to the statements made in the context of the first aspect of the invention, second aspect of the invention, and third aspect of the invention. The statements made therein in relation to the cell-free combination, especially to the first component, to the crosslinkable albumin, to the second component, and to the crosslinking agent, the hydrogel-forming material or hydrogel, and also in relation to the kit or multicomponent system are also valid mutatis mutandis for the medical product or the pharmaceutical formulation according to the fourth aspect of the invention.

A fifth aspect of the invention relates to a discharge device which comprises a cell-free combination according to the first aspect of the invention, a hydrogel-forming material or hydrogel according to the second aspect of the invention, or a medical product or a pharmaceutical formulation according to the fourth aspect of the invention.

The discharge device may comprise a twin-chamber syringe or dual-chamber syringe (single-piston syringe with two compartments separated from one another via a liquid-permeable membrane or a liquid-permeable diaphragm) and especially a mixing facility. The mixing facility is preferably designed to bring about mixing, especially homogeneous mixing, of the first component and the second component of the cell-free combination. As a result it is possible with particular advantage to ensure that there is sufficient crosslinking of the albumin with the crosslinking agent as early as during discharge. The discharge device may further comprise a cannula, which may be in fluid-conducting communication with a discharge aperture of the discharge device, especially of the mixing facility.

With regard to further features and advantages of the discharge device, reference is made completely, in order to avoid unnecessary repetition, to the statements made in the context of the first aspect of the invention, second aspect of the invention, third aspect of the invention, and fourth aspect of the invention. The statements made therein in relation to the cell-free combination, especially to the first component, to the crosslinkable albumin, to the second component, and to the crosslinking agent, the hydrogel-forming material or hydrogel, the kit or multicomponent system, and also in relation to the medical product or the pharmaceutical formulation are also valid mutatis mutandis for the discharge device according to the fifth aspect of the invention.

According to a sixth aspect, the invention relates to the use of a cell-free combination
  for producing a formulation in hydrogel form, especially depot formulation in hydrogel form,
  and/or
  for coating a medical product, especially implant, preferably with a formulation in hydrogel form, especially depot formulation in hydrogel form,
wherein the cell-free combination comprises a first component and a second component, the first component comprising crosslinkable albumin and the second component comprising a crosslinking agent for the albumin.

Regarding further features and advantages of the use, reference is made entirely to the statements made in the context of the first aspect of the invention. The statements made therein in relation to the cell-free combination, especially to the first component, to the crosslinkable albumin, to the second component, and to the crosslinking agent are also valid mutatis mutandis for the use according to the sixth aspect of the invention.

According to a seventh aspect, the invention relates to the use of a hydrogel-forming material or hydrogel
  for producing a formulation in hydrogel form, especially depot formulation in hydrogel form,
  and/or
  for coating a medical product, especially implant, preferably with a formulation in hydrogel form, especially depot formulation in hydrogel form,
wherein the hydrogel-forming material or hydrogel comprises a cell-free combination according to the first aspect of the invention or consists of a cell-free combination according to the first aspect of the invention, or is produced or producible by mixing of the first component and of the second component of the cell-free combination according to the first aspect of the invention.

Regarding further features and advantages of the use, reference is made entirely to the statements made in the context of the first aspect of the invention and second aspect of the invention. The statements made therein in relation to the cell-free combination, especially to the first component, to the crosslinkable albumin, to the second component, and to the crosslinking agent, and also in relation to the hydrogel-forming material or hydrogel, are also valid mutatis mutandis for the use according to the seventh aspect of the invention.

Further features and advantages of the invention are apparent from the description hereinafter of preferred embodiments in the form of examples. Here, individual features may each be realized alone or in combination with one another. The preferred embodiments serve merely for further elucidation and for better understanding of the invention, without limiting it thereto.

EXAMPLES SECTION

Figure 1:
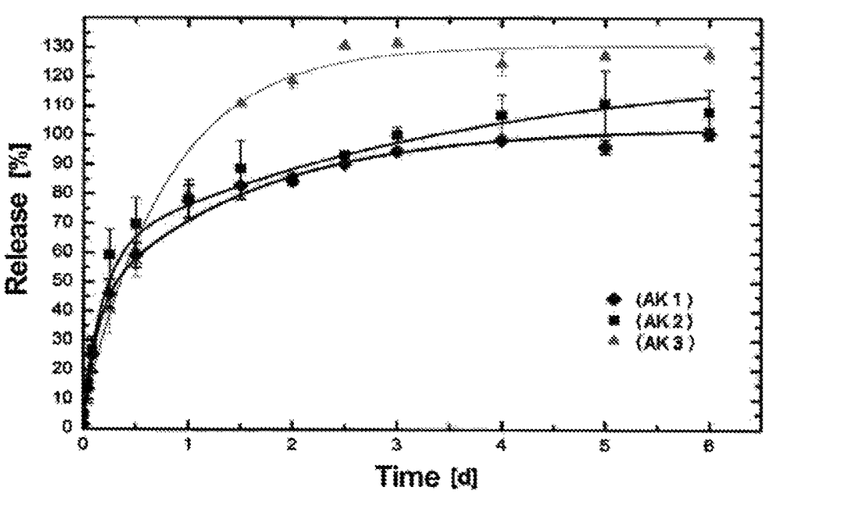
FIG. 1 shows restricted release profiles of AK1, AK2 and AK3.

1. Production of Antibody-Loaded Hydrogels
Component A:
containing antibody 1 (AK1): A homogeneous mixture was prepared from 0.525 ml of a solution of maleimide-functionalized albumin (44 mmol/L maleimide groups, 2.4 mmol/L albumin, loading level 18.3 maleimide functions per albumin molecule), 1 ml of hyaluronic acid solution (20 mg/ml, MW 1.5 MDa), and 1.475 ml of PBS. This mixture was admixed with 1000 µl of the antibody solution (144 kDa, 145 mg/ml) and in turn mixed homogeneously.
containing antibody 2 (AK2): A homogeneous mixture was prepared from 0.525 ml of a solution of maleimide-functionalized albumin (44 mmol/L maleimide groups, 2.4 mmol/L albumin, loading level 18.3 maleimide functions per albumin molecule), 1 ml of hyaluronic acid solution (20 mg/ml, MW 1.5 MDa), and 1.475 ml of PBS. This mixture was admixed with 1000 µl of the antibody solution (149 kDa, 115 mg/ml) and in turn mixed homogeneously.
containing antibody 3 (single-domain antibody, AK3): A homogeneous mixture was prepared from 0.525 ml of a solution of maleimide-functionalized albumin (44 mmol/L maleimide groups, 2.4 mmol/L albumin, loading level 18.3 maleimide functions per albumin molecule), 1 ml of hyaluronic acid solution (20 mg/ml, MW 1.5 MDa), and 1.475 ml of PBS. This mixture was admixed with 1000 µl of the antibody solution (42 kDa, 38 mg/ml) and in turn mixed homogeneously.
Component B:
Bisthio-polyethylene glycol (MW 10 kDa) was dissolved in 0.9% NaCl solution, which had been adjusted to a pH of 3-4 using 10% HCl, to give a thiol group concentration of 22.5 mmol/L. The thiol concentration was determined by Ellman assay (molar extinction coefficient used: 14 150).
Hydrogel:
For release studies, components A and B were crosslinked to hydrogels with a double-piston syringe surmounted with mixing device in a ratio of 4:1 (4 parts component A, 1 part component) in situ in a stainless steel mold to form cylindrical moldings with a volume of 1 ml (H~ 5 mm, D~ 16 mm). The moldings were transferred after 30 minutes from the mold into the release apparatus.
2. Release Studies
The hydrogel moldings were incubated in 100 ml of PBS (50 ml in the case of AK3) in closed glass bottles at 37° C. in a water bath. Using a sampler, samples of 1 ml were taken at intervals (increasing from 1 h to 24 h) through a tube inserted with tight sealing through the lid of the bottles. The study period up to the last measurement point was 6 days. The amount of released antibody in solution was determined by means of UV spectrophotometry at 280 nm, employing the corresponding molar extinction coefficient. The release profiles of AK1, AK2, and AK3 are shown in FIG. 1. The graph illustrates the significantly retarded release of the antibodies from the hydrogel moldings into the PBS solution. The ordinate of the graph has been standardized to the percentage of antibody released in total into the solution, in relation to the total amount of antibody present in the hydrogel molding at the time TO.

The invention claimed is:

1. A method for decelerating or retarding release of active ingredient, wherein a cell-free combination in the form of a kit is used, wherein the cell-free combination comprises a first component and a second component, the first component comprising crosslinkable albumin and the second component comprising a crosslinking agent for the albumin, wherein the crosslinkable albumin is functionalized by groups and wherein the crosslinkable albumin has a degree of functionalization of 5 groups to 35 groups per albumin molecule.

2. The method of claim 1, wherein the combination is used for surgical administration or surgical injection.

3. The method of claim 1, wherein the crosslinkable albumin is a functionalized albumin, the albumin being functionalized with groups which are selected from the group consisting of maleimide groups, vinyl sulfone groups, acrylate groups, alkyl halide groups, azirine groups, pyridyl groups, thionitrobenzoic acid groups, arylating groups, and combinations of at least two of the stated groups.

4. The method of claim 1, wherein the crosslinkable albumin is maleimide-functionalized albumin.

5. The method of claim 1, wherein the crosslinkable albumin has a fraction of 0.1 wt % to 11 wt %, based on the total volume of the cell-free combination.

6. The method of claim 1, wherein the crosslinking agent comprises nucleophilic groups.

7. The method of claim 6, wherein the crosslinking agent has a degree of functionalization of at least 2 groups.

8. The method of claim 1, wherein the crosslinking agent is selected from the group consisting of thiol-functionalized polyethylene glycol, thiol-functionalized hyaluronic acid, thiol-functionalized starch, thiol-functionalized dextran, thiol-functionalized polyvinyl alcohol, thiol-functionalized polyvinylpyrrolidone, and mixtures of at least two of the stated crosslinking agents.

9. The method of claim 1, wherein the crosslinking agent has a fraction of 0.1 wt % to 30 wt %, based on the total volume of the cell-free combination.

10. The method of claim 1, wherein the first component and/or the second component further comprise an active ingredient.

11. The method of claim 10, wherein the active ingredient is selected from the group consisting of peptide, protein, therapeutic protein, antibody or antibody fragment, immunosuppressant, cytokine, growth factor, chemokine, differentiation factor, modulation factor, immunostimulant, hormone, cytostatic agent or chemotherapeutic agent, anti-inflammatory, analgesic, chondroprotective agent, antibiotic, polysaccharide, lipid, DNA, RNA, siRNA, agent for gene therapy, and mixtures of at least two of the stated active ingredients.

12. The method of claim 1, wherein the first component and/or the second component are present as a lyophilized solid.

13. The method of claim 1, wherein the first component and the second component are present spatially separate from one another.

14. The method of claim 1, wherein the combination is used for surgical administration or surgical injection into a joint.

15. The method of claim 14, wherein the joint is a knee joint.

16. The method of claim 1, wherein the combination is used for surgical administration or surgical injection into a tissue cavity.

17. The method of claim 16, wherein the tissue cavity is a tissue cavity resulting from tumor removal.

18. The method of claim 4, wherein the maleimide-functionalized albumin is maleimide-functionalized serum albumin.

19. The method of claim 18, wherein the maleimide-functionalized serum albumin is of human origin.

20. The method of claim 6, wherein the nucleophilic groups are thiol and/or thiolate groups.

21. The method of claim 1, wherein the crosslinking agent is selected from the group consisting of thiolate-functionalized polyethylene glycol, thiolate-functionalized hyaluronic acid, thiolate-functionalized starch, thiolate-functionalized dextran, thiolate-functionalized polyvinyl alcohol, thiolate-functionalized polyvinylpyrrolidone, and mixtures of at least two of the stated crosslinking agents.

22. The method of claim 8, wherein the thiol-functionalized polyethylene glycol is dithio-polyethylene glycol.

* * * * *